US010510918B2

(12) United States Patent
Hu et al.

(10) Patent No.: US 10,510,918 B2
(45) Date of Patent: Dec. 17, 2019

(54) ENDOSCOPE IMAGING MODULE

(71) Applicant: FUJIKURA LTD., Koto-ku, Tokyo (JP)

(72) Inventors: Wei-Zhi Hu, Sakura (JP); Kenichi Nakatate, Sakura (JP); Takeshi Segi, Sakura (JP); Kenichi Ishibashi, Sakura (JP); Fumihiko Nishimura, Sakura (JP); Satoshi Hida, Sakura (JP); Hitoe Iikura, Sakura (JP); Hideo Shiratani, Sakura (JP)

(73) Assignee: FUJIKURA LTD., Tokyo (JP)

( * ) Notice: Subject to any disclaimer, the term of this patent is extended or adjusted under 35 U.S.C. 154(b) by 1043 days.

(21) Appl. No.: 14/275,214

(22) Filed: May 12, 2014

(65) Prior Publication Data

US 2014/0249368 A1    Sep. 4, 2014

Related U.S. Application Data

(63) Continuation of application No. PCT/JP2012/079522, filed on Nov. 14, 2012.

(30) Foreign Application Priority Data

Nov. 15, 2011  (JP) ................................. 2011-249755

(51) Int. Cl.
  *H01L 31/18* (2006.01)
  *A61B 1/05* (2006.01)
  (Continued)

(52) U.S. Cl.
  CPC ............ *H01L 31/18* (2013.01); *A61B 1/0011* (2013.01); *A61B 1/04* (2013.01); *A61B 1/051* (2013.01);
  (Continued)

(58) Field of Classification Search
  CPC . H01L 2224/73265; H01L 2224/32225; H01L 2224/48247; H01L 2924/00;
  (Continued)

(56) References Cited

U.S. PATENT DOCUMENTS 5,056,503 A * 10/1991 Nagasaki ........... A61B 1/00179
                                                      600/104
5,220,198 A    6/1993 Tsuji
(Continued)

FOREIGN PATENT DOCUMENTS

CN    101672980 A    3/2010
CN    101808568 A    8/2010
(Continued)

OTHER PUBLICATIONS

Machine Translation of JP 09-307087 of record May 12, 2014.
(Continued)

*Primary Examiner* — John P Leubecker
*Assistant Examiner* — Shankar Raj Ghimire
(74) *Attorney, Agent, or Firm* — Sughrue Mion, PLLC

(57) ABSTRACT

An endoscope includes: an imaging device chip having a chip connection portion; a tubular housing tube used to a scope tip portion of an endoscope; a substrate to which the imaging device chip is fixed, the substrate having a substrate connection portion, the substrate being capable of bending at near the substrate connection portion when the substrate is inserted into the housing tube; a lead wire connecting the substrate connection portion and the chip connection portion; flexible and non-conductive resin covering an entirety of the lead wire; and an imaging module including the substrate provided with the imaging device chip thereon, the imaging module inserted into the housing tube.

3 Claims, 4 Drawing Sheets

(51) Int. Cl.
- *A61B 1/00* (2006.01)
- *H04N 5/225* (2006.01)
- *A61B 1/04* (2006.01)
- *H01L 31/0203* (2014.01)
- *G02B 23/24* (2006.01)

(52) U.S. Cl.
CPC ..... *G02B 23/2423* (2013.01); *G02B 23/2484* (2013.01); *H01L 31/0203* (2013.01); *H04N 5/2253* (2013.01); *H01L 2224/45124* (2013.01); *H01L 2224/45144* (2013.01); *H01L 2224/45147* (2013.01); *H01L 2224/48091* (2013.01); *H01L 2224/49109* (2013.01); *H01L 2224/49175* (2013.01); *H01L 2224/8592* (2013.01); *H04N 2005/2255* (2013.01)

(58) Field of Classification Search
CPC .......... H01L 2224/8592; H04N 5/2257; H04N 2005/2255; H04N 5/2251; H04N 5/2253; A61B 2562/164; A61B 1/05; A61B 1/041; A61B 1/051; A61B 2562/166; A61B 1/0011; A61B 1/04; A61B 1/00009; A61B 1/00018; G02B 23/2423; G02B 23/2484
USPC ....... 600/109, 110; 348/65, 76; 438/26, 106, 438/126
See application file for complete search history.

(56) References Cited

U.S. PATENT DOCUMENTS

| | | | |
|---|---|---|---|
| 5,418,566 A * | 5/1995 | Kameishi | A61B 1/042 348/294 |
| 6,417,885 B1 | 7/2002 | Suzuki et al. | |
| 7,564,111 B2 * | 7/2009 | Sawahata | H01L 27/14618 257/432 |
| 7,773,122 B2 * | 8/2010 | Irion | H04N 5/2251 348/222.1 |
| 7,775,971 B2 * | 8/2010 | Fujimori | A61B 1/04 600/110 |
| 8,189,062 B2 * | 5/2012 | Irion | H04N 5/2251 348/222.1 |
| 8,821,382 B2 * | 9/2014 | Kagawa | A61B 1/051 348/76 |
| 8,858,425 B2 * | 10/2014 | Farr | A61B 1/00103 600/109 |
| 2002/0080233 A1 * | 6/2002 | Irion | H04N 5/2251 348/65 |
| 2005/0119527 A1 * | 6/2005 | Banik | A61B 1/00059 600/117 |
| 2006/0104581 A1 * | 5/2006 | Nakatate | C03B 37/15 385/116 |
| 2006/0249737 A1 * | 11/2006 | Fujimori | H01L 23/481 257/79 |
| 2006/0264704 A1 * | 11/2006 | Fujimori | A61B 1/04 600/101 |
| 2007/0120050 A1 * | 5/2007 | Sawahata | H01L 27/14618 250/239 |
| 2008/0023784 A1 | 1/2008 | Nakayama | |
| 2008/0058601 A1 * | 3/2008 | Fujimori | A61B 1/041 600/167 |
| 2008/0100732 A1 * | 5/2008 | Minamio | H04N 5/2251 348/294 |
| 2009/0027491 A1 * | 1/2009 | Irion | H04N 5/2251 348/65 |
| 2009/0268019 A1 * | 10/2009 | Ishii | A61B 1/00124 348/65 |
| 2010/0063361 A1 | 3/2010 | Kuchimaru et al. | |
| 2010/0155739 A1 * | 6/2010 | Kuramoto | C08G 59/3245 257/76 |
| 2010/0231702 A1 | 9/2010 | Tsujimura et al. | |
| 2011/0199473 A1 * | 8/2011 | Kojima | A61B 1/05 348/76 |
| 2011/0245600 A1 | 10/2011 | Ishii et al. | |
| 2011/0249106 A1 * | 10/2011 | Makino | H04N 5/2254 348/76 |
| 2012/0197081 A1 | 8/2012 | Kimura | |
| 2013/0107025 A1 | 5/2013 | Kuchimaru | |
| 2015/0358518 A1 * | 12/2015 | Ishii | A61B 1/00124 600/109 |
| 2016/0080704 A1 * | 3/2016 | Nakamura | H04N 7/183 348/76 |

FOREIGN PATENT DOCUMENTS

| | | |
|---|---|---|
| JP | 61-50544 A | 3/1986 |
| JP | 61-254917 A | 11/1986 |
| JP | 09-069983 A | 3/1997 |
| JP | 09-307087 A | 11/1997 |
| JP | 2001-051210 A | 2/2001 |
| JP | 2001-053988 A | 2/2001 |
| JP | 3216650 B2 | 10/2001 |
| JP | 2005-295050 A | 10/2005 |
| JP | 2006-167282 A | 6/2006 |
| JP | 2011-212161 A | 10/2011 |
| JP | 2012-157472 A | 8/2012 |

OTHER PUBLICATIONS

Machine Translation of JP 2011-212161 of record May 12, 2014.
Machine Translation of JP 2012-157472 of record May 12, 2014.
Machine Translation of JP 2006-167282 of record May 12, 2014.
Machine Translation of JP 2001-053988 of record May 12, 2014.
Machine Translation of JP 2001-051210 of record May 12, 2014.
Machine Translation of JP 09-069983 of record May 12, 2014.
Machine Translation of JP 2005-295050 of record May 12, 2014.
Communication dated Sep. 10, 2013 from the Japanese Patent Office in counterpart application No. 2011-249755.
Communication dated Jul. 28, 2015 from the State Intellectual Property Office of the People's Republic of China in counterpart application No. 201280053046.9.
Communication dated Jul. 9, 2015 from the European Patent Office in counterpart European Application No. 12849196.6.
International Search Report for PCT/JP2012/079522 dated Jan. 22, 2013.
Japanese Office Action for JP 2011-249755 dated Jun. 18, 2013.

* cited by examiner

ENDOSCOPE IMAGING MODULE

CROSS REFERENCE TO RELATED APPLICATIONS

This application is a continuation application based on a PCT Patent Application No. PCT/JP2012/079522, filed Nov. 14, 2012, whose priority is claimed on Japanese Patent Application No. 2011-249755 filed on Nov. 15, 2011, the content of which is hereby incorporated by reference.

BACKGROUND OF THE INVENTION

Field of the Invention

The present invention relates to an imaging device-packaging method to mount an imaging device chip which is provided in a tip portion of an endoscope on a flexible substrate. Further, the present invention relates to an endoscope-assembling method using the above packaging method, an imaging module, and an endoscope.

Description of Related Art

An endoscope (an electronic endoscope) is known of a type in which an imaging device is provided in a tip portion of the endoscope, wiring is drawn out from the imaging element, and image information is converted into an electric signal which is then transmitted. In such an endoscope, a substrate with the imaging device mounted thereon is inserted into a tubular scope tip portion (refer to, for example, Patent Documents 1 to 3 (Japanese Patent No. 3216650 (hereinafter, Patent Document 1), Japanese Unexamined Patent Application, First Publication No. S61-50544 (hereinafter, Patent Document 2), Japanese Unexamined Patent Application, First Publication No. S61-254917 (hereinafter, Patent Document 3)).

In Patent Document 1 (refer to Paragraphs 0032 to 0045, in particular, Paragraphs 0033 and 0044), an electronic endoscope is described in which an imaging device is mounted on a central plane portion of a flexible circuit board bent into a U-shape and the diameter of an insertion portion is reduced.

In Patent Document 2, an endoscope is described which has an imaging device electrically connected to one end portion of a bent flexible printed circuit board and is accommodated in a tubular body.

In Patent Document 3, an endoscope is described in which a prism is directly bonded to an element surface of an imaging device without interposing a cover glass therebetween.

In the endoscopes described in Patent Documents 1 and 2, the imaging device is mounted on the flexible board. In Patent Document 1, if wire bonding is used for electric connection of the flexible board and the imaging device, it is necessary to increase the size of the endoscope (refer to Paragraph 0008 of Patent Document 1), and thus the imaging device and the flexible board are connected by a method to reduce the size of the endoscope, such as performing conductive connection by a lead frame in a state where the flexible board with the imaging device mounted thereon is bent (refer to Paragraphs 0035 and 0040 of Patent Document 1).

In the endoscope described in Patent Document 2, although there is no clear statement in the specification, according to FIG. 2 of Patent Document 2, it is considered to be a structure in which an image element chip is packaged, similar to FIG. 17 of Patent Document 1.

In the endoscope described in Patent Document 3, wiring is directly connected to an input-output terminal of the imaging device.

SUMMARY OF THE INVENTION

The present invention has been made in view of the above circumstances and has an object to provide an imaging device chip-packaging method in which it is possible to reduce the diameter of an endoscope with a simpler configuration, an endoscope-assembling method using the packaging method, an imaging module, and an endoscope.

In order to solve the above problems, according to a first aspect of the invention, an endoscope is provided, the endoscope including: an imaging device chip having a chip connection portion; a tubular housing tube used to a scope tip portion of an endoscope; a substrate to which the imaging device chip is fixed, the substrate having a substrate connection portion, the substrate being capable of bending at near the substrate connection portion when the substrate is inserted into the housing tube; a lead wire connecting the substrate connection portion and the chip connection portion; flexible and non-conductive resin covering an entirety of the lead wire; and an imaging module including the substrate provided with the imaging device chip thereon, the imaging module being inserted into the housing tube.

According to a second aspect of the invention, an imaging module inserted into a tubular housing tube in a scope tip portion of an endoscope is provided, the imaging module including: an imaging device chip having a chip connection portion; a substrate to which the imaging device chip is fixed, the substrate having a substrate connection portion, the substrate being capable of bending at near the substrate connection portion when the substrate is inserted into the housing tube; a lead wire connecting the substrate connection portion and the chip connection portion; and flexible and non-conductive resin covering an entirety of the lead wire.

According to a third aspect of the invention, a method of assembling an endoscope is provided, the method including: preparing an imaging device chip having a chip connection portion, a tubular housing tube used as a scope tip portion of an endoscope, and a substrate having a substrate connection portion, the substrate being capable of bending at near the substrate connection portion when the substrate is inserted into the housing tube; fixing the imaging device chip to the substrate; connecting the substrate connection portion and the chip connection portion by a lead wire; covering an entirety of the lead wire with flexible and non-conductive resin; bending the substrate, to which the imaging device chip is fixed, at near the substrate connection portion, and thereby inserting the substrate into the housing tube.

In the third aspect of the invention, it is preferable that the substrate connection portion be arranged in a direction along a longitudinal direction of the scope tip portion with respect to the chip connection portion; and the substrate be bent at near the substrate connection portion to be directed to directed to the longitudinal direction, and thereby the substrate be inserted into the housing tube.

In the third aspect of the invention, it is preferable that the substrate connection portion have a first substrate connection portion and a second substrate connection portion, the chip connection portion have a first chip connection portion and a second chip connection portion, the lead wire have a first lead wire and a second lead wire, the method further includes: arranging the first substrate connection portion in a direction along a longitudinal direction of the scope tip portion with respect to the first chip connection portion; arranging the second substrate connection portion in a direction orthogonal to the longitudinal direction of the scope tip portion with respect to the second chip connection portion; connecting the first substrate connection portion and the first chip connection portion by the first lead wire; covering an entirety of the first lead wire with flexible and non-conductive resin, connecting the second substrate connection portion and the second chip connection portion by the second lead wire, covering an entirety of the second lead wire with flexible and non-conductive resin, and bending the substrate at near the second substrate connection portion to be directed to the orthogonal direction, thereby inserting the substrate into the housing tube.

According to a fourth aspect of the invention, a method of packaging an imaging device chip inserted into a tubular housing tube in a scope tip portion of an endoscope is provided, the method including: preparing an imaging device chip having a chip connection portion, and a substrate having a substrate connection portion, the substrate being capable of bending at near the substrate connection portion when the substrate is inserted into the housing tube; fixing the imaging device chip to the substrate; connecting the substrate connection portion and the chip connection portion by a lead wire; and covering an entirety of the lead wire with flexible and non-conductive resin.

In the fourth aspect of the invention, it is preferable that the substrate connection portion be arranged in a direction along a longitudinal direction of the scope tip portion with respect to the chip connection portion.

In the fourth aspect of the invention, it is preferable that the substrate connection portion have a first substrate connection portion and a second substrate connection portion, the chip connection portion have a first chip connection portion and a second chip connection portion, the lead wire have a first lead wire and a second lead wire, the method further includes: arranging the first substrate connection portion in a direction along a longitudinal direction of the scope tip portion with respect to the first chip connection portion, arranging the second substrate connection portion in a direction orthogonal to the longitudinal direction of the scope tip portion with respect to the second chip connection portion, connecting the first substrate connection portion and the first chip connection portion by the first lead wire, covering an entirety of the first lead wire with flexible and non-conductive resin, connecting the second substrate connection portion and the second chip connection portion by the second lead wire, and covering an entirety of the second lead wire with flexible and non-conductive resin.

According to the first to fourth aspects of the invention, since the substrate is capable of bending at near the connection portion of the substrate, it is possible to insert the substrate into a scope tip portion having a smaller diameter, and thus it is possible to reduce the diameter of an endoscope with a simpler configuration.

DETAILED DESCRIPTION OF THE INVENTION

Hereinafter, the invention will be described based on preferred embodiments with reference to the drawings.

Figure 1A:
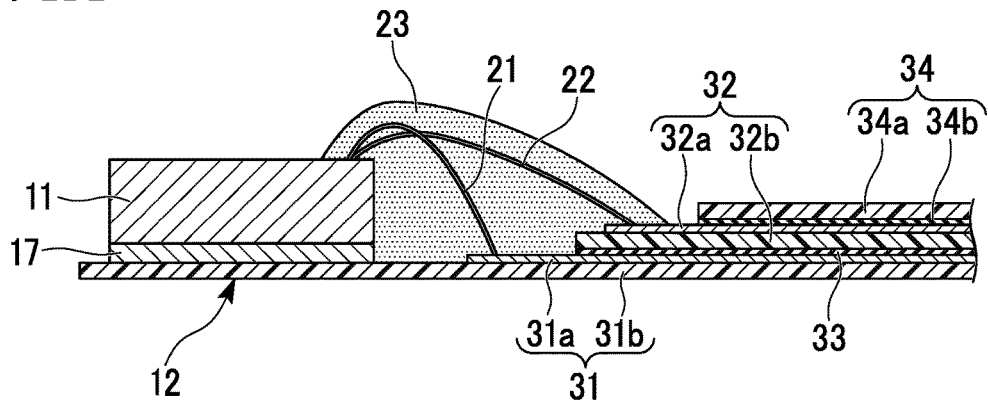
FIG. 1A is a cross-sectional view showing a first embodiment of a substrate with an imaging device chip mounted thereon according to the invention.
Figure 1B:
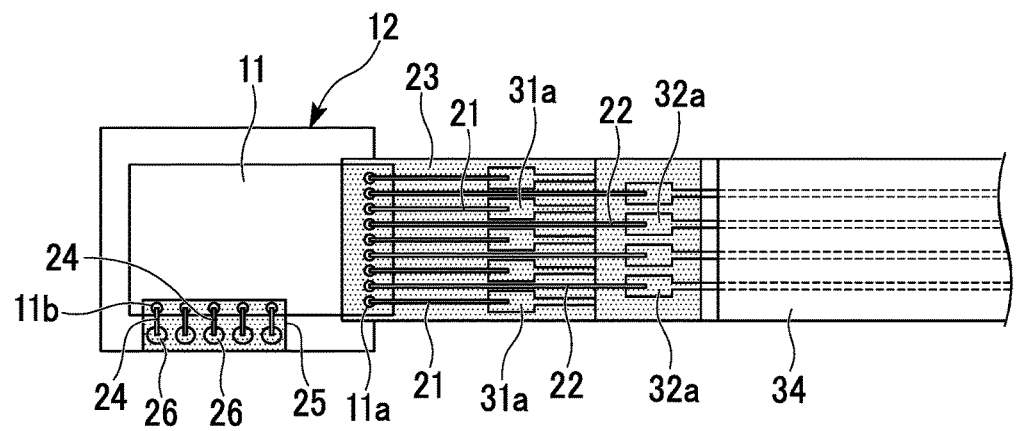
FIG. 1B is a plan view showing the first embodiment of the substrate with the imaging device chip mounted thereon according to the invention.

FIGS. 1A and 1B show a first embodiment of a substrate 12 with an imaging device chip 11 mounted thereon according to the invention.

As the imaging device chip 11, although it is not particularly limited, a semiconductor chip such as a CMOS (complementary metal oxide semiconductor), a CCD (charge-coupled device), or a CPD (charge priming device) can be provided. The size of the chip is not particularly limited. However, in order to reduce the diameter of a tube which is used in an endoscope, it is preferable to adopt a small-sized chip, and it is also possible to use a chip having sides (a long side and a short side) less than or equal to about 2 mm and a thickness less than or equal to about 0.5 mm, for example.

Figure 4A:
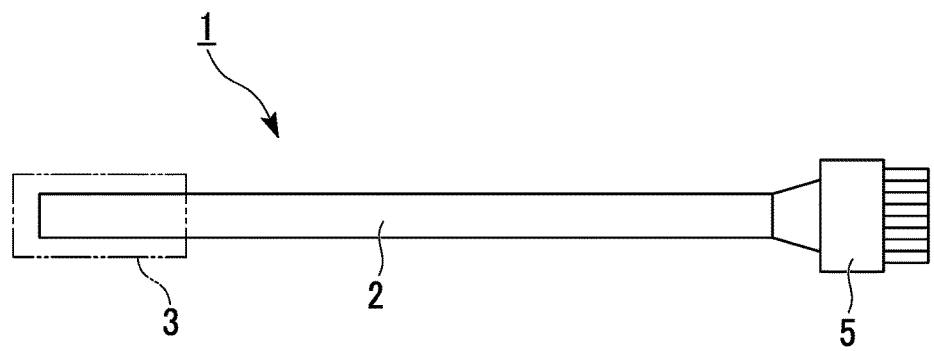
FIG. 4A is a plan view showing an example of an endoscope.
Figure 4B:
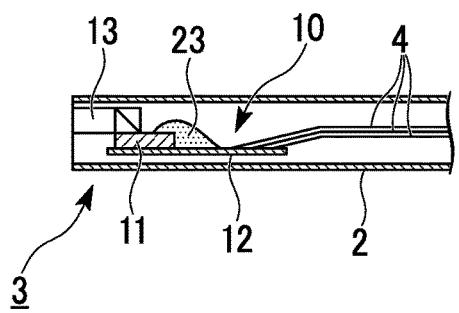
FIG. 4B is a cross-sectional view showing an example of a scope tip portion.
Figure 5:
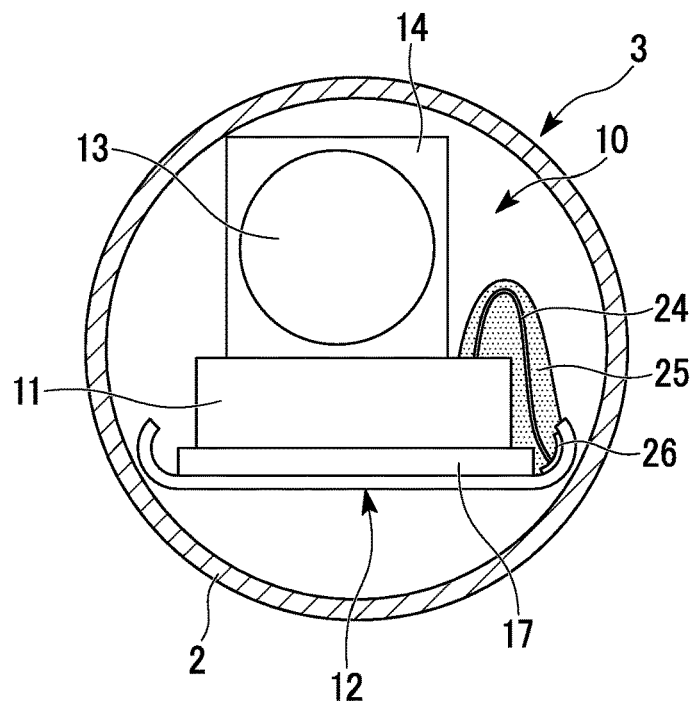
FIG. 5 is a front view showing an example in which the imaging module of FIG. 2 is inserted into the scope tip portion.

As for the substrate 12, a flexible substrate is used such that it is possible to bend the substrate 12 when the substrate 12 is inserted into a tubular housing tube 2 in a scope tip portion 3 of an endoscope 1, as shown in FIGS. 4B and 5.

As the flexible substrate 12, a flexible wiring board (FPC) with a metal layer such as copper foil formed on one face or both faces of a flexible insulating film, or a laminated wiring board in which two or more FPCs are laminated is preferable. As the insulating film, polyimide, polyester, liquid crystal polymer, or the like can be used. However, it is not particularly limited thereto. For example, it is possible that the thickness of the substrate 12 is set to be in a range of 50 to 200 µm, for example.

In the case of the first embodiment, a plurality of FPCs 31 and 32 respectively using insulating films 31b and 32b as base materials is laminated with an adhesive layer 33 interposed therebetween, and connection portions (first substrate connection portions) 31a and 32a formed by patterning metal layers of the FPCs 31 and 32 are formed to be divided into two layers. In this way, it is possible to secure the large areas of the connection portions (the first substrate connection portions) 31a and 32a of the substrate 12, compared to a pitch of a connection portion (a first chip connection portion) 11a of the imaging device chip 11. A coverlay 34 (a protective film) in which an adhesive layer 34b is formed on one face of an insulating film 34a is laminated on the FPC 32 of the uppermost layer.

In a method of packaging the imaging device chip 11 according to the first embodiment, first, the imaging device chip 11 is fixed to the substrate 12. A member fixing the imaging device chip 11 to the substrate 12 is not particularly limited, and a jointing material 17 such as an adhesive, solder, or silver solder, a mechanical member such as a screw, or the like can be used appropriately.

After the fixation of the imaging device chip 11, the connection portions (the first chip connection portions) 11a of the imaging device chip 11 and the connection portions (the first substrate connection portions) 31a and 32a of the substrate 12 are connected by lead wires (first lead wires) 21 and 22. Furthermore, connection portions (second chip connection portions) 11b of the imaging device chip 11 and connection portions (second substrate connection portions) 26 of the substrate 12 are connected by lead wires (second lead wires) 24. The connection portions 11a and 11b are terminals such as bumps formed on the upper surface of the imaging device chip 11. Furthermore, the connection portions 31a, 32a, and 26 of the substrate 12 are terminals such as pads formed at wirings of the substrate 12. As the lead wires 21, 22, and 24, for example, a gold (Au) wire, an aluminum (Al) wire, a copper (Cu) wire, or the like can be used.

At the time of the connection using the lead wires 21, 22, and 24, the substrate 12 may have a shape arbitrarily determined depending on an imaging module of an endoscope, for example, a planar shape. For this reason, it is possible to efficiently proceed with work by using an automatic wire-bonding apparatus.

In the case of the first embodiment, the imaging device chip 11 has the first connection portions (the first chip connection portions) 11a arranged along the short side which is located at an end (the right side in FIG. 1B) in a longitudinal direction of the scope tip portion 3, and the second connection portions (the second chip connection portions) 11b arranged along the long side which is located at an end (the lower side in FIG. 1B) orthogonal to the longitudinal direction of the scope tip portion 3.

The connection portions of the substrate 12 have the first connection portions (the first substrate connection portions) 31a and 32a which are located in a direction (in FIG. 1B, the right-and-left direction) along the longitudinal direction of the scope tip portion 3 with respect to the first connection portions (the first chip connection portions) 11a of the imaging device chip 11, and the second connection portions (the second substrate connection portions) 26 which are located in a direction (in FIG. 1B, the up-and-down direction) orthogonal to the longitudinal direction of the scope tip portion 3 with respect to the second connection portions (the second chip connection portions) 11b of the imaging device chip 11.

The first connection portions (the first chip connection portions) 11a of the imaging device chip 11 and the first connection portions (the first substrate connection portions) 31a and 32a of the substrate 12 are connected by the first lead wires 21 and 22 extending substantially in the direction along the longitudinal direction of the scope tip portion 3.

Furthermore, the second connection portions (the second chip connection portions) 11b of the imaging device chip 11 and the second connection portions (the second substrate connection portions) 26 of the substrate 12 are connected by the second lead wires 24 extending substantially in the direction orthogonal to the longitudinal direction of the scope tip portion 3.

In this way, even if the imaging device chip 11 is provided with a large number of connection portions 11a and 11b and the first connection portions 11a and the second connection portions 11b are provided along two orthogonal sides of the imaging device chip 11, the respective lead wires 21, 22, and 24 can be electrically connected to the wires on the substrate 12 without being congested.

After the first chip connection portions and the first substrate connection portions are connected by the lead wires 21 and 22, the entirety of the lead wires 21 and 22 is covered with flexible and non-conductive resin 23. Furthermore, after the second chip connection portions and the second substrate connection portions are connected by the lead wires 24, the entirety of the lead wires 24 is covered with flexible and non-conductive resin 25. In this way, the contact between the lead wires 21, 22, and 24 adjacent to each other is prevented, and thus it is possible to prevent electrical short-circuit. Furthermore, coverings by the resins 23 and 25 include the connection portions 31a, 32a, and 26 of the substrate 12 and the connection portions 11a and 11b of the imaging device chip 11, whereby connection places between these connection portions and the lead wires 21, 22, and 24 are also protected, and thus durability is improved.

Figure 2:
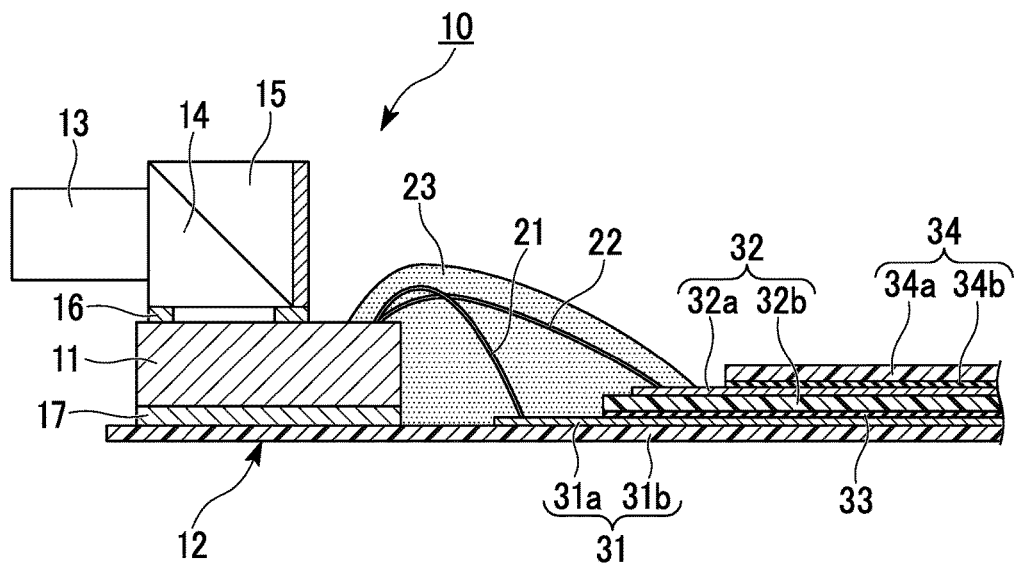
FIG. 2 is a cross-sectional view showing an example of an imaging module in which a lens and a prism are provided on the imaging device chip of FIGS. 1A and 1B.

An imaging module 10 according to the first embodiment shown in FIG. 2 is provided with a prism 14 fixed onto the imaging device chip 11 and an objective lens 13 mounted on the prism 14, as an optical system for forming an optical image on an imaging area of the imaging device chip 11. The prism 14 has a supporting member 15 mounted thereon and is fixed to a periphery 16 of the imaging area in the imaging device chip 11 by an adhesive or the like.

Figure 8:
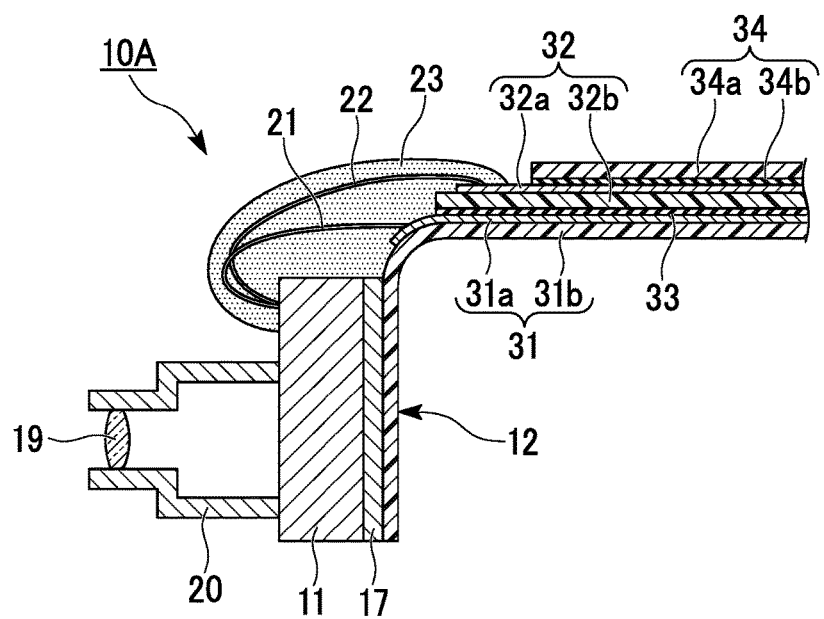
FIG. 8 is a cross-sectional view showing an example of an imaging module in which a lens is provided on the imaging device chip of FIGS. 7A and 7B.

The objective lens 13 may be a column-shaped gradient index lens (GRIN lens) and may also have a structure in which a lens 19 is mounted in a frame 20, as shown in FIG. 8.

In addition, mounting of the prism 14 or the objective lens 13 may be performed after the imaging device chip 11 is mounted on the substrate 12 and may be performed before the imaging device chip 11 is mounted on the substrate 12.

According to the method of packaging the imaging device chip 11 related to the first embodiment, since the connection portions 31a and 32a of the substrate 12 and the connection portions 11a of the imaging device chip 11 are connected by the flexible lead wires 21 and 22 and an area between the connection portions 31a and 32a of the substrate 12 and the connection portions 11a of the imaging device chip 11 is covered with the flexible and non-conductive resin 23, it is possible to bend the substrate 12.

In addition, since the connection portions 26 of the substrate 12 and the connection portions 11b of the imaging device chip 11 are connected by the flexible lead wires 24 and an area between the connection portions 26 of the substrate 12 and the connection portions 11b of the imaging device chip 11 is covered with the flexible and non-conductive resin 25, it is possible to bend the substrate 12.

In the case of the imaging module 10 according to the first embodiment, it is possible to bend the substrate 12 to be directed to the longitudinal direction between the first connection portions (the first substrate connection portions) 31a and 32a of the substrate 12 and the first connection portions (the first chip connection portions) 11a of the imaging device chip 11 (at an area which includes the first substrate connection portions and the first chip connection portions, at near the first substrate connection portions) (refer to FIG. 8). In addition, it is possible to bend the substrate 12 to be directed to the direction orthogonal to the longitudinal direction between the second connection portions (the second substrate connection portions) 26 of the substrate 12 and the second connection portions (the second chip connection portions) 11*b* of the imaging device chip 11 (at an area which includes the second substrate connection portions and the second chip connection portions, at near the second substrate connection portions).

It is preferable that the flexible and non-conductive resins 23 and 25 exhibit a property such as a rubber form, a clay form, a gel form, a jelly form, a semi-solid form, a paste form, a slurry form, or a liquid form, for example, and have low viscosity (for example, in a range of 1000 cP to 10000 cP) having fluidity of a degree capable of being applied. It is also possible to perform a process such as curing or drying after application, and in this case, it is favorable if resin after curing or drying has flexibility.

The imaging module 10 shown in FIG. 2 can be used while being inserted into the housing tube 2 in the scope tip portion 3 of the endoscope 1, as shown in FIG. 4B. The flexible substrate 12 may be connected to an electric signal line 4 such as a cord or a cable on the way. In the endoscope 1 shown in FIG. 4A, a connector (an electric connector) 5 is provided at an end portion on the side where an operator manipulates the endoscope 1, and the electric signal line 4 is electrically connected to a terminal (not shown) in the connector 5. In this way, it is possible to connect the electric signal line 4 of the endoscope 1 to an image display device such as a video processor or a personal computer immediately.

As the electric signal line 4, although it is not particularly limited, an ultrafine coaxial cable (for example, a coaxial cable in which the size of a central conductor is less than or equal to 36 in AWG (American Wire Gauge) standard) is preferable. As the connector 5, although it is not particularly limited, various standards such as a USB (Universal Serial Bus) are widely known and any of them can be suitably used in the invention.

Figure 3:
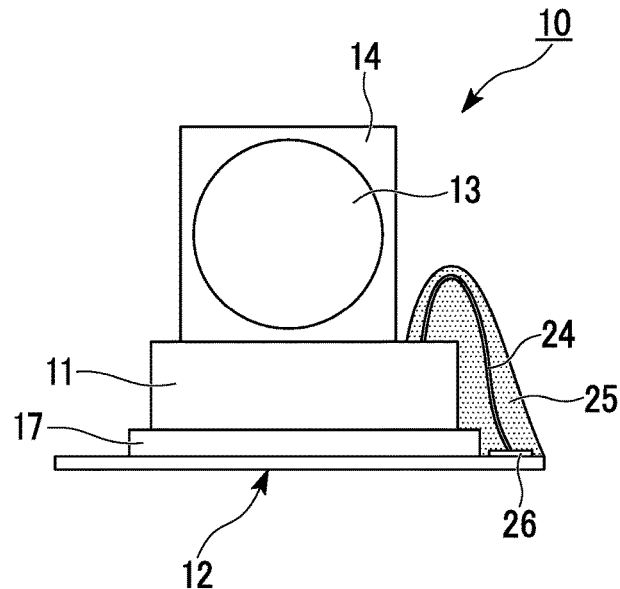
FIG. 3 is a front view when the imaging module of FIG. 2 is viewed from the side facing the lens.

FIG. 5 shows a state where the substrate 12 of the imaging module 10 is inserted into the housing tube 2 while bending the substrate 12 to be directed to a direction orthogonal to the longitudinal direction of the scope tip portion 3. The substrate 12 is inserted into the housing tube 2 along with the lead wires 24 connected to the second connection portions 26 of the substrate 12, while bending the substrate 12 to be directed to the direction orthogonal to the longitudinal direction (in FIG. 5, a direction perpendicular to the plane of paper) of the scope tip portion 3. In this way, compared to a case where a substrate is not bent, the width of the substrate 12 in the direction orthogonal to the longitudinal direction of the scope tip portion 3 can be reduced, and thus it is possible to use the housing tube 2 having a smaller inner diameter. In addition, in the imaging module 10 before it is inserted into the housing tube 2, the substrate 12 may be flat, as shown in FIG. 3.

In the first embodiment, since an optical path changing member such as a prism is provided on the imaging module 10 and the imaging area of the imaging module 10 is directed in the direction (in FIG. 5, an upward direction) orthogonal to the longitudinal direction of the scope tip portion 3, even if the inner diameter of the housing tube 2 is slightly larger than the length of a side of the imaging device chip 11, the insertion of the imaging module 10 becomes possible. That is, in the first embodiment of the invention, it is possible to use a housing tube having a small inner diameter. On the other hand, as in Patent Document 1 (Japanese Patent No. 3216650), in a case where the imaging area of the imaging module 10 is directed in the longitudinal direction of the scope tip portion 3, in order to accommodate the imaging device chip 11, the inner diameter of the housing tube 2 needs to be larger than the length of a diagonal of the imaging device chip 11 (the length of a diagonal of the imaging device chip 11 when the imaging device chip 11 is viewed from above, as shown in FIG. 1B).

Figure 6:
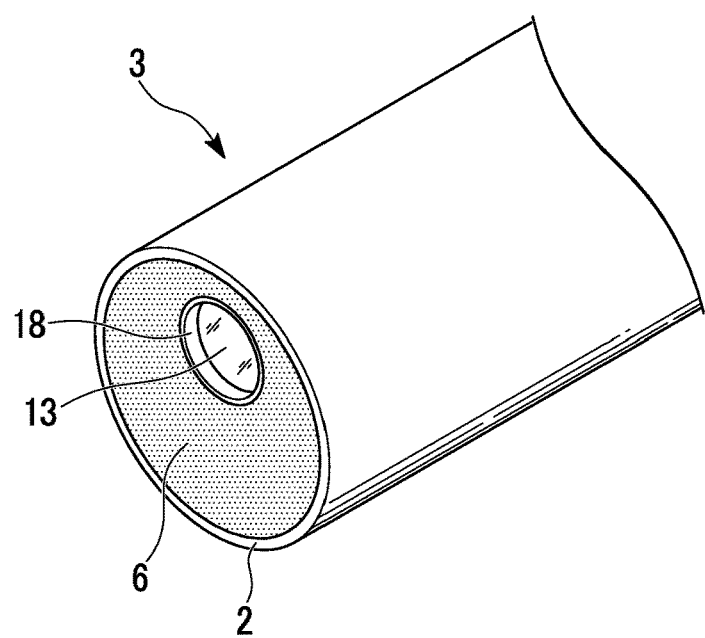
FIG. 6 is a perspective view showing an example in which the scope tip portion of FIG. 5 is sealed with resin.

FIG. 6 shows a state where a tip portion of the housing tube 2 is sealed with a sealing material 6 after the imaging module 10 is inserted into the housing tube 2. The objective lens 13 is exposed at the scope tip portion 3. In order to prevent the sealing material 6 from invading onto the object plane of the objective lens 13, it is also possible to make a configuration so as to dam up the sealing material 6 by making an end portion of a tube 18 protrude around the objective lens 13.

The invention has been described above based on the preferred first embodiment. However, the invention is not limited to the first embodiment described above and various modifications are possible within a scope which does not depart from the invention.

Figure 7A:
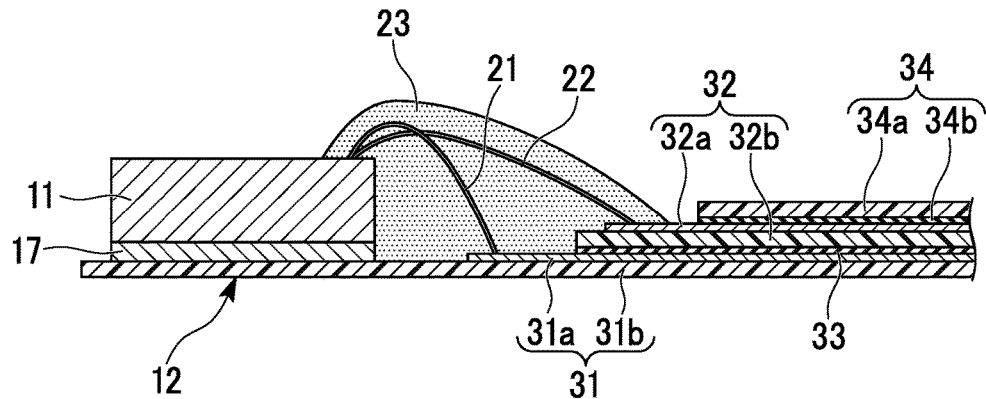
FIG. 7A is a cross-sectional view showing a second embodiment of the substrate with the imaging device chip mounted thereon according to the invention.
Figure 7B:
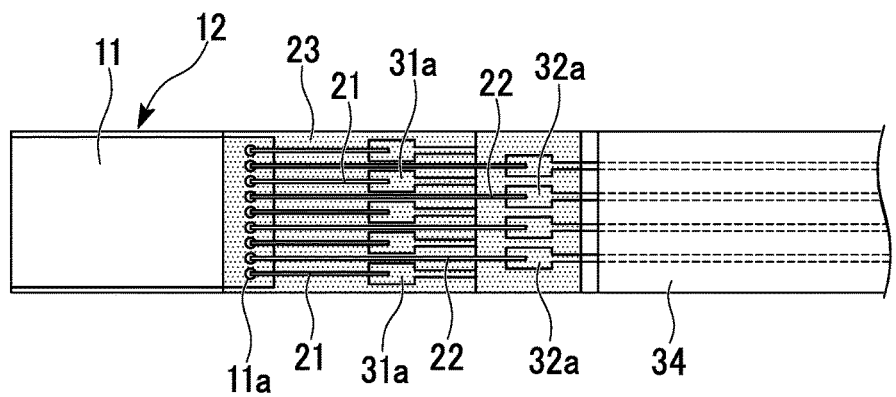
FIG. 7B is a plan view showing the second embodiment of the substrate with the imaging device chip mounted thereon according to the invention.

FIGS. 7A and 7B show a second embodiment of the substrate 12 with the imaging device chip 11 mounted thereon, in the invention.

In the case of the second embodiment, the connection portions 31*a* and 32*a* of the substrate 12 are located in the direction (in FIG. 7B, the right-and-left direction) along the longitudinal direction of the scope tip portion 3 with respect to the connection portions 11*a* of the imaging device chip 11. The connection portions 11*a* of the imaging device chip 11 and the connection portions 31*a* and 32*a* of the substrate 12 are connected by the lead wires 21 and 22 extending substantially in the direction along the longitudinal direction of the scope tip portion 3.

In a method of packaging the imaging device chip 11 according to the second embodiment, similar to the first embodiment, the imaging device chip 11 is fixed to the substrate 12, the connection portions 31*a* and 32*a* of the substrate 12 and the connection portions 11*a* of the imaging device chip 11 are connected by the lead wires 21 and 22, and thereafter, the entirety of the lead wires 21 and 22 is covered with the flexible and non-conductive resin 23.

In this way, the contact between the lead wires 21 and 22 adjacent to each other is prevented, and thus it is possible to prevent electrical short-circuit. Furthermore, a covering by the resin 23 includes the connection portions 31*a* and 32*a* of the substrate 12 and the connection portions 11*a* of the imaging device chip 11, whereby connection places between these connection portions and the lead wires 21 and 22 are also protected, and thus durability is improved.

Furthermore, since the connection portions 31*a* and 32*a* of the substrate 12 and the connection portions 11*a* of the imaging device chip 11 are connected by the flexible lead wires 21 and 22 and an area between the connection portions 31*a* and 32*a* of the substrate 12 and the connection portions 11*a* of the imaging device chip 11 (an area which includes the substrate connection portions and the chip connection portions, at near the substrate connection portions) is covered with the flexible and non-conductive resin 23, it is possible to bend the substrate 12.

In this way, in comparison with a method in which the connection of a lead frame is performed in a state where a connection substrate is bent, as described in Paragraph 0040 of Patent Document 1 (Japanese Patent No. 3216650), in the second embodiment, the connections of the flexible lead wires 21 and 22 are possible with the flexible substrate 12 being flat, and thus it is possible to improve productivity.

In an imaging module 10A according to a third embodiment shown in FIG. 8, as an optical system for forming an optical image on the imaging area of the imaging device chip 11, the lens 19 is mounted in the frame 20 and then fixed onto the imaging device chip 11.

In the imaging module 10A according to the third embodiment, it is possible to insert the substrate 12 into a housing tube (not shown) in a scope tip portion of an endoscope while bending the substrate 12 to be directed to the longitudinal direction between the first connection portions 31a and 32a of the substrate 12 and the connection portions 11a of the imaging device chip 11 (at an area which includes the substrate connection portions and the chip connection portions, in near the substrate connection portions).

A method of configuring an endoscope by using the imaging module 10A according to a fourth embodiment can be carried out in the same manner as in the case using the imaging module 10 according to the first embodiment. For example, as shown in FIG. 6, it is also possible to seal the tip portion of the housing tube around the objective lens by using a sealing material after the imaging module is inserted into the housing tube.

According to the imaging module 10A related to the fourth embodiment, since it is possible to bend the substrate 12 even after the connection portions 31a and 32a of the substrate 12 and the connection portions 11a of the imaging device chip 11 are connected and covered with the resin 23, it is possible to insert the substrate 12 into the scope tip portion having a smaller diameter, and thus it is possible to reduce the diameter of the endoscope with a simpler configuration.

What is claimed is:

1. An endoscope comprising:
    an imaging device chip having a chip connection portion;
    a tubular housing tube used in a scope tip portion of an endoscope;
    a laminated substrate to which the imaging device chip is fixed, the laminated substrate having a first layer and a second layer provided on the first layer, the laminated substrate having a first substrate connection portion, and a second substrate connection portion, the laminated substrate being capable of bending near the first substrate connection portion and the second substrate connection portion when the laminated substrate is inserted into the housing tube;
    a first lead wire connecting the first substrate connection portion and the chip connection portion;
    a second lead wire connecting the second substrate connection portion and the chip connection portion;
    a flexible and non-conductive resin covering an entirety of the first lead wire and an entirety of the second lead wire, the flexible and non-conductive resin covering the first substrate connection portion, the second substrate connection portion, and the chip connection portion; and
    an imaging module comprising the laminated substrate provided with the imaging device chip thereon, the imaging module being inserted into the housing tube,
    wherein the first substrate connection portion is provided on the first layer, wherein the second substrate connection portion is provided on the second layer, and wherein the first substrate connection portion and the second substrate connection portion are arranged at different positions along a longitudinal direction of the scope tip portion.

2. The endoscope according to claim 1, wherein the laminated substrate is capable of bending between the chip connection portion and each of the first substrate connection portion and the second substrate connection portion when the laminated substrate is inserted into the housing tube.

3. An imaging module inserted into a tubular housing tube in a scope tip portion of an endoscope, comprising:
    an imaging device chip having a chip connection portion;
    a laminated substrate to which the imaging device chip is fixed, the laminated substrate having a first layer and a second layer provided on the first layer, the laminated substrate having a first substrate connection portion and a second substrate connection portion, the laminated substrate being capable of bending near the first substrate connection portion and the second substrate connection portion when the laminated substrate is inserted into the housing tube;
    a first lead wire connecting the first substrate connection portion and the chip connection portion;
    a second lead wire connecting the second substrate connection portion and the chip connection portion; and
    a flexible and non-conductive resin covering an entirety of the first lead wire and an entirety of the second lead wire, the flexible and non-conductive resin covering the first substrate connection portion, the second substrate connection portion, and the chip connection portion
    wherein the first substrate connection portion is provided on the first layer, wherein the second substrate connection portion is provided on the second layer, and wherein the first substrate connection portion and the second substrate connection portion are arranged at different positions along a longitudinal direction of the scope tip portion.

* * * * *